United States Patent [19]

Lundquist et al.

[11] Patent Number: 5,531,686

[45] Date of Patent: Jul. 2, 1996

[54] CATHETER STEERING MECHANISM

[75] Inventors: Ingemar Lundquist, Pebble Beach; Russell B. Thompson, San Leandro, both of Calif.

[73] Assignee: EP Technologies, Inc., Sunnyvale, Calif.

[21] Appl. No.: 363,294

[22] Filed: Dec. 23, 1994

Related U.S. Application Data

[63] Continuation of Ser. No. 99,603, Jul. 30, 1993, Pat. No. 5,395,327, which is a continuation of Ser. No. 991,474, Dec. 16, 1992, Pat. No. 5,254,088, which is a continuation of Ser. No. 736,384, Jul. 26, 1991, abandoned, which is a division of Ser. No. 473,667, Feb. 2, 1990, abandoned.

[51] Int. Cl.$^6$ .................................................. A61M 37/00
[52] U.S. Cl. .......................................... 604/95; 604/282
[58] Field of Search .............................. 604/95, 104, 107, 604/170, 281, 282; 128/656–658, 772

[56] References Cited

U.S. PATENT DOCUMENTS

| | | |
|---|---|---|
| 2,498,692 | 2/1950 | Mains . |
| 3,470,876 | 10/1969 | Barchilon . |
| 3,500,820 | 3/1970 | Almen . |
| 3,521,620 | 7/1970 | Cook . |
| 3,528,406 | 9/1970 | Jeckel et al. . |
| 3,605,725 | 9/1971 | Bentou . |
| 3,625,200 | 12/1971 | Muller . |
| 3,773,034 | 11/1973 | Burns et al. . |
| 4,273,111 | 6/1981 | Tsukaya . |
| 4,543,090 | 9/1985 | McCoy . |
| 4,582,181 | 4/1986 | Samson . |
| 4,586,923 | 5/1986 | Gould et al. . |
| 4,641,649 | 2/1987 | Walinsky et al. . |
| 4,643,720 | 2/1987 | Lanciano . |
| 4,719,924 | 1/1988 | Crittenden et al. . |
| 4,723,936 | 2/1988 | Buchbinder et al. . |
| 4,740,195 | 4/1988 | Lanciano . |
| 4,758,221 | 7/1988 | Jureidini . |

(List continued on next page.)

FOREIGN PATENT DOCUMENTS 1213571  3/1966  Germany .

OTHER PUBLICATIONS

Smith et al., "Preliminary Report on New Method of Intestinal Intubation with the Aid of a Flexible Stylet with a Controllable Tip", Surgery, vol. 27, No. 6, Jun. 1950, pp. 817–821.

Lenox Flexile Borescopes Article (Undated).

*Primary Examiner*—John D. Yasko
*Assistant Examiner*—Adam J. Cermak
*Attorney, Agent, or Firm*—Ryan, Maki, Mann & Hohenfeldt

[57] ABSTRACT

A steering mechanism including a steering shaft coupled to a controller which includes a handle and apparatus for manipulating the distal end of the steering shaft. The steering shaft includes a flexible coiled spring having a lead spring fixed in position with respect to a distal end thereof in the distal end of the steering shaft. One or more steering wires is affixed at the distal ends thereof to the lead spring. The steering wires extend through the steering shaft to the controller, and the steering apparatus of the controller is used to place tension on one or both of the steering wires. The attachment of the distal ends of the steering wires to the lead spring may be opposite one another or may be offset for providing greater maneuverability. Tension may be placed on the steering wires by wedges mounted transversely to the controller housing, or by rotation of a shaft mounted transversely to the controller housing, the steering wires being attached to the shaft such that rotation in one direction tenses one steering wire, and rotation in the other direction tenses the other steering wire. Two independently rotatable shafts may be used to separately control the two steering wires.

The steering shaft is adapted for insertion into a lumen of a catheter for use in guiding the distal end of the catheter to a treatment site within a patient. The steering mechanism may also be used in conjunction with tools or apparatus which must reach into difficult locations, such as engines or other machines.

7 Claims, 7 Drawing Sheets

U.S. PATENT DOCUMENTS

| | | |
|---|---|---|
| 4,826,087 | 5/1989 | Chinery . |
| 4,838,859 | 6/1989 | Strassmann . |
| 4,886,067 | 12/1989 | Palermo . |
| 4,921,482 | 5/1990 | Hammerslag et al. . |
| 4,934,340 | 6/1990 | Ebling et al. . |
| 4,934,380 | 6/1990 | de Toledo . |
| 4,944,727 | 7/1990 | McCoy . |
| 4,984,581 | 1/1991 | Stice . |
| 4,985,022 | 1/1991 | Fearnot . |
| 5,037,391 | 8/1991 | Hammerslag et al. . |
| 5,055,101 | 10/1991 | McCoy . |

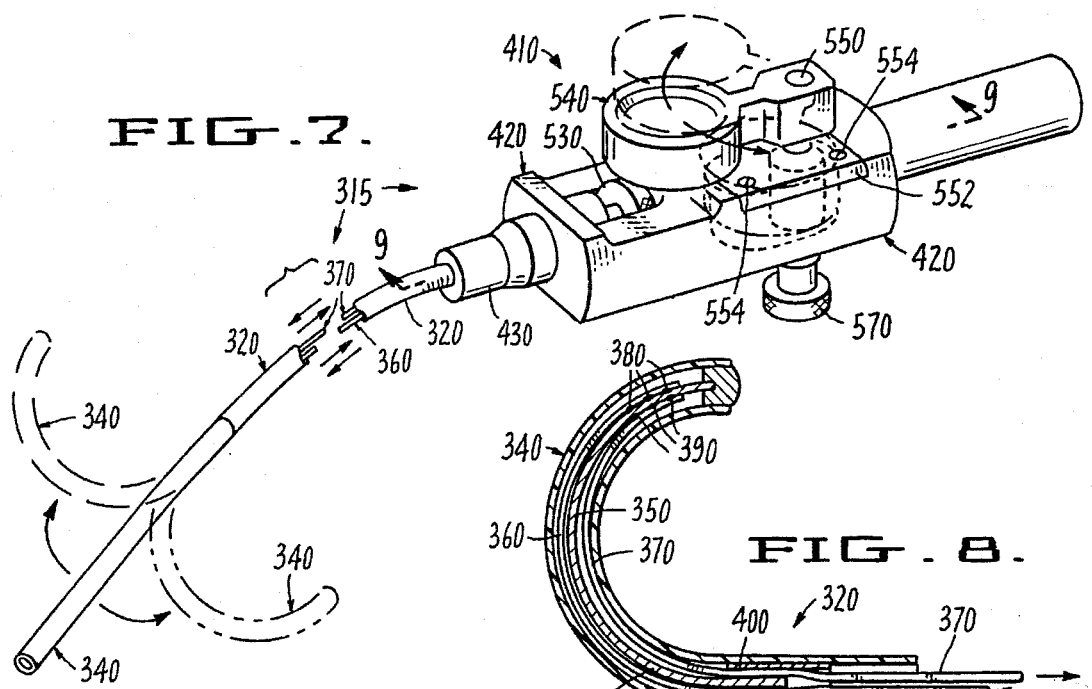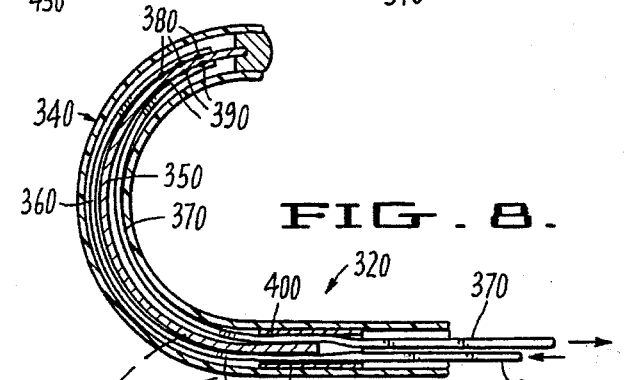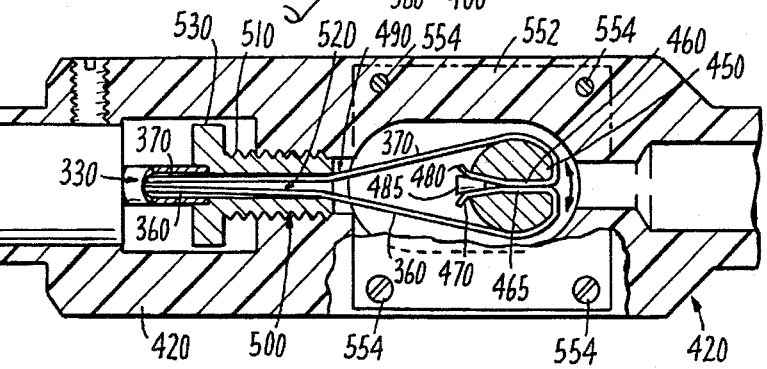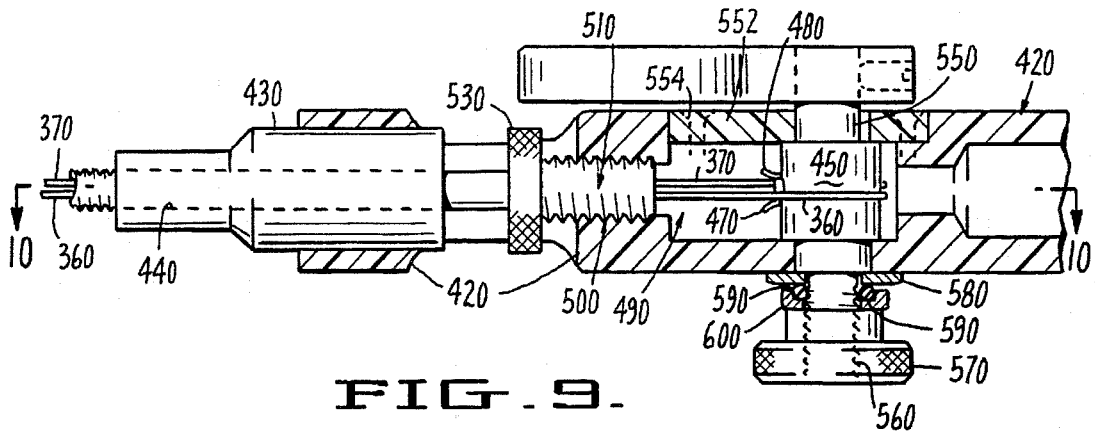

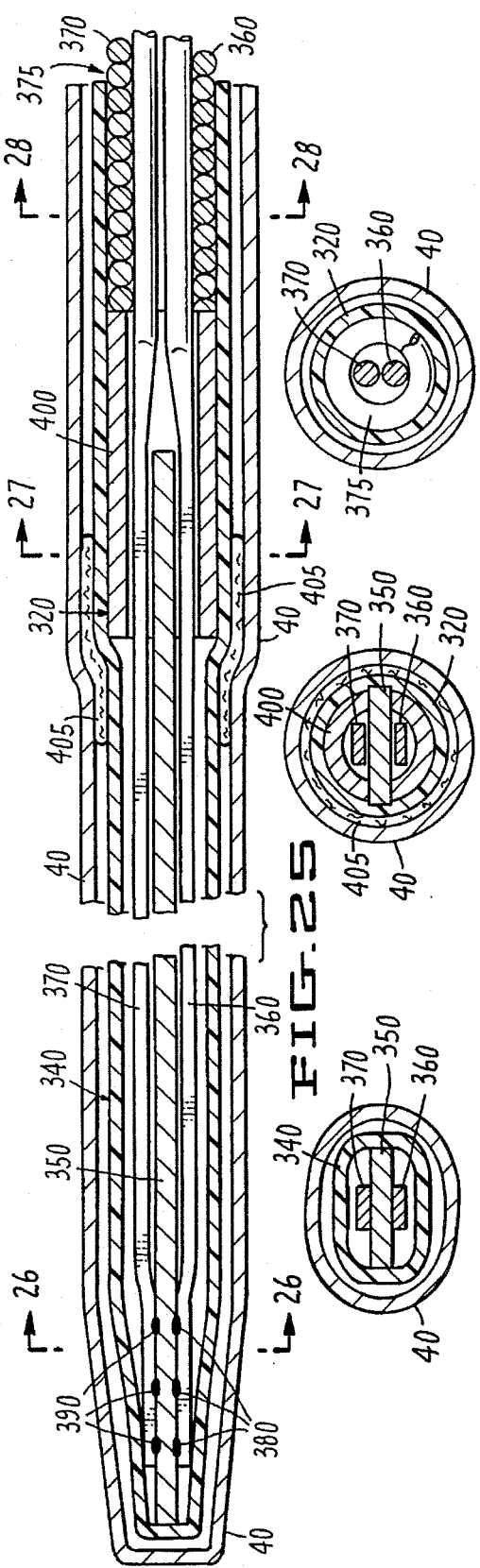

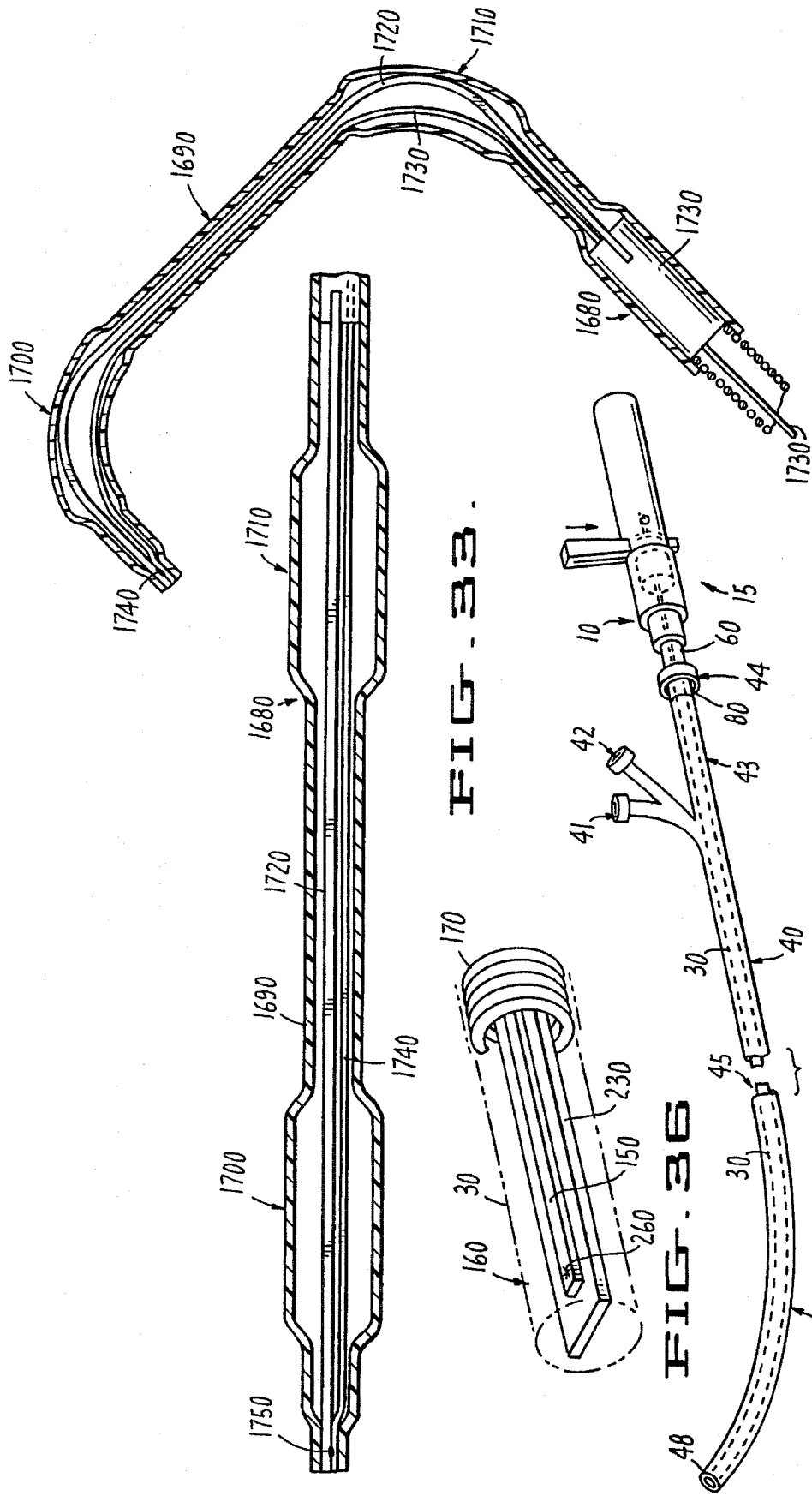

CATHETER STEERING MECHANISM

This is a continuation of application(s) Ser. No. 08/099,603 filed on Jul. 30, 1993, now U.S. Pat. No. 5,395,327, which is a continuation of application Ser. No. 07/991,474 filed Dec. 16, 1992, now U.S. Pat. No. 5,254,088, which is a continuation of application Ser. No. 07/736,384 filed Jul. 26, 1991 (abandoned), which is a divisional of application Ser. No. 07/473,667 filed Feb. 2, 1990 (abandoned).

BACKGROUND OF THE INVENTION

This invention relates to a steering mechanism for use with medical catheters or other devices which need to be positioned in difficult locations.

In many medical procedures, it is necessary to position a catheter at a location within a patient's body. A typical emplacement for the distal end of a catheter might be within a ventricle of the heart, by way of the femoral vein. In so passing a catheter through the femoral vein, it is necessary to avoid obstructions, vessel junctions and the like, and to make sharp turns to position the distal end of the catheter within the ventricle. Other medical procedures involve similar difficulties in placing a catheter.

In conventional catheters used today, the tip of the catheter may be bent, or may include a stylet which is bent, such that a semipermanent curve is given to the distal end of the catheter so that a physician may guide the distal end thereof towards the treatment location. A disadvantage with this type of apparatus is that the curvature of the bend is not adjustable while the catheter is in the body, and any change in the curvature requires the physician to remove the catheter and reshape the distal end.

There is a need for a steering mechanism for catheters and other devices wherein the distal end of the device can be manipulated at Will from a location outside the patient's body or outside the apparatus in which the device is placed. Accordingly, it is an object of the present invention to provide such a steering mechanism, and in particular to provide such a mechanism which provides a wide range of steerability.

It is another object of the invention to provide such a mechanism which may be completely manipulated with one hand.

It is a further object of the invention to provide such a steering mechanism wherein the distal end of the mechanism may be bent into varying shapes for placement in different positions while the mechanism is in use.

Other objects and advantages will more fully appear in the course of the following discussion.

SUMMARY OF THE INVENTION

The steering mechanism of the invention includes a flexible steering shaft attached to a controller. The controller includes a handle with a central bore in which one or more steering wires are carried. The steering shaft includes a flexible coil, at the distal end of which a ferrule is positioned. Mounted on the ferrule is a lead spring, which extends to the distal tip of the steering shaft. The steering wire has a distal end which is welded or otherwise affixed to the distal end of the lead spring. Tension may be placed on the steering wire by manipulating the controller, thus turning the distal end of the steering shaft.

In use, the steering shaft is inserted into a lumen of a catheter, and the controller is manipulated to turn the distal end of the catheter.

In a preferred embodiment, two steering wires are provided, one attached to each side of the lead spring at the distal end of the steering shaft. The two steering wires may be attached at points directly opposite one another on the lead spring, or they may be offset to provide for different configurations of the distal end of the steering shaft when tension is placed on one, the other, or both steering wires.

In one embodiment, the controller includes a wedge mounted transversely to the handle of the controller, the wedge receiving the steering wire and being tapered such that pushing the wedge in one direction places tension on the steering wire, and pushing it in the other direction releases tension from the steering wire. In a two steering wire embodiment, two wedges are provided, positioned such that their tapered portions run opposite to one another, for providing two-way steering of the distal end of the steering shaft.

In another embodiment of the invention, two steering wires may be attached to a rotatable shaft which is mounted on an axis transverse to a longitudinal axis of the handle of the controller. A central knob is attached to the shaft, such that turning it one way places tension on one of the steering wires and turning it the other way places tension on the other steering wire.

In an alternative embodiment of the invention, the two steering wires are attached to two separate rotatable shafts mounted on the controller, and the shafts may be independently rotated for independent control of the steering wires.

In a preferred embodiment of the invention, regions of the steering shaft at the distal end thereof are enlarged in diameter to allow for greater bending of the distal end at those regions.

Variations on these and other embodiments are described below.

BRIEF DESCRIPTION OF THE DRAWINGS

FIG. 7 is a perspective view of an alternative embodiment of the invention.

FIG. 8 is a sectional view of a distal end of the embodiment of FIG. 7.

FIG. 9 is a sectional view taken along line 9—9 of FIG. 7.

FIG. 10 is a sectional view taken along line 10—10 of FIG. 9.

FIG. 25 is a sectional view of an alternative embodiment to the distal end of a steering mechanism of the invention.

FIG. 26 is a sectional view taken along line 26≦26 of FIG. 25.

FIG. 27 is a sectional view taken along line 27—27 of FIG. 25.

FIG. 28 is a sectional view taken along line 28—28 of FIG. 25.

FIG. 29 is an exploded view showing detail of a portion of the invention.

FIG. 30 is a sectional view of a portion of the steering mechanism of the invention.

FIG. 31 is a sectional view taken along line 31—31 of FIG. 30.

FIG. 32 is a sectional view taken along line 32—32 of FIG. 30.

FIGS. 33 and 34 are sectional views of an alternative embodiment of the invention.

FIG. 35 shows the embodiment of FIG. 1 in use with a conventional medical catheter.

FIG. 36 shows an alternative embodiment to the distal tip of the invention.

DESCRIPTION OF THE PREFERRED EMBODIMENTS

Figure 1:
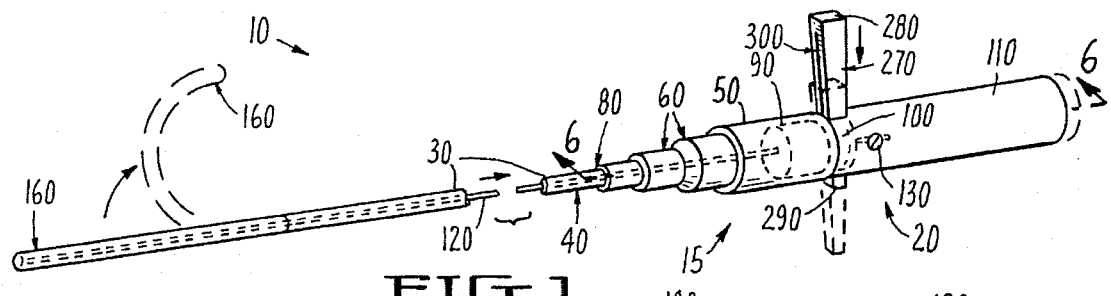
FIG. 1 shows a steering mechanism of the invention.

FIG. 1 shows a steering mechanism 10 including a controller 15 with a handle 20. A flexible steering shaft 30 is attached at its proximal end 40 to the controller 15. The shaft 30 is formed from any conventional material which is flexible, slightly elastic to tolerate bending without permanent deformation, and biocompatible for applications in the medical field. Preferably, the shaft 30 is formed from TEFLON (tetrafluoroethylene) for minimizing friction with other elements of the apparatus.

The mechanism 10 may be used to steer and position many different types of apparatus, and the embodiment shown in FIG. 1 is adapted for use with medical catheters.

As shown in FIG. 35, the steering shaft 30 is positioned within a lumen 45 of a catheter 40, the distal tip 48 of the catheter 40 is maneuvered to a desired position within a patient's body, and the steering mechanism may then be removed so that the lumen 45 may then be used by the physician for introduction of treatment drugs or the like to the patient. The catheter may include also conventional ports for this purpose, such as ports 41 and 42 shown in FIG. 35 which communicate with one or more additional lumens (not separately shown) within the catheter 40.

The catheter 40 is any standard catheter, such as an angioplasty catheter (for laser angioplasty, balloon angioplasty, or other treatments), a catheter with pacing and/or sensing probes, or indeed any flexible or steerable device which one may wish to introduce into a place which is difficult to reach. Such devices need not be confined to the medical field. Other important applications include the introduction of tools (for inspection, adjustment, or repair) into engines or other machines, and the manipulation of objects in any type of conduit. For inspection purposes, fiber optics may be carried by the catheter 40 or other device. In machine repair and adjustment applications, any convention tool may be attached to the distal end of the steering shaft 30, such as drill bits, clamps, wrenches, grinders, and so on, and these tools may be remotely operated from the controller 15. Thus, although the present embodiments of the invention are described primarily in terms of use with a catheter, the invention has many other applications.

In the course of the following discussion, it will be understood that the manipulation, steering or positioning of the shaft 30 (or other shafts of the alternative embodiments) results in concomitant manipulation, steering or positioning of the catheter or other device with which the steering mechanism is used. Any of the following embodiments may be used with the catheter 40 shown in FIG. 35 or other steerable device.

Figure 6:
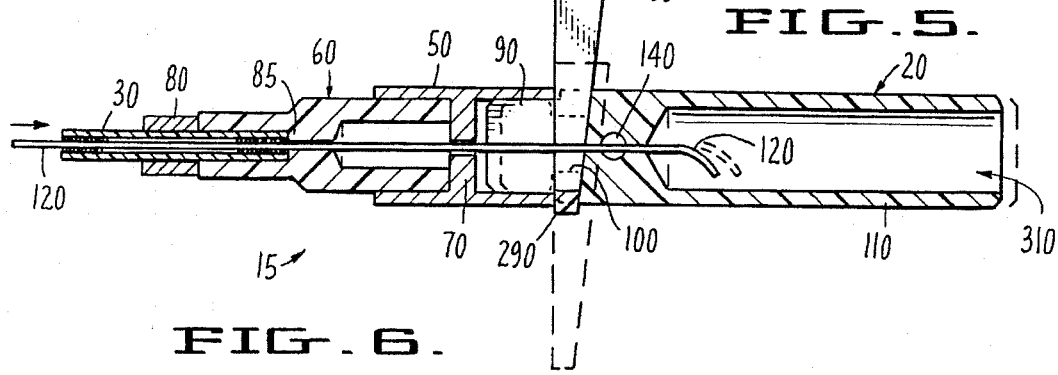
FIG. 6 is a sectional view taken along line 6—6 of FIG. 1.

The steering mechanism 10 includes a first sleeve 50, as shown in FIGS. 1 and 6, adjacent which is positioned a second sleeve 60. The sleeve 50 includes a stop 70 at its interior, as shown in FIG. 6, against which the second sleeve 60 abuts. The second sleeve 60 has an outer diameter closely matching the inner diameter of the first sleeve 50.

A third sleeve 80 is positioned within a forward portion of the second sleeve 60, and has an outer diameter closely matching the inner diameter of the forward portion. The third sleeve 80 has an inner diameter closely matching the outer diameter of the steering shaft 30. The sleeves 50, 60 and 80 are firmly fixed so that they do not move relative to one another. As shown in FIG. 6, the steering shaft 30 is seated against a shoulder 85 of the sleeve 60. The sleeve 60 acts as a cable or wire retainer for the steering wire 120.

Alternatively, for ease of manufacture the sleeves 50, 60 and 80 may be of a unitary design.

As shown in FIG. 35, the catheter 40 includes a proximal end 43 which fits tightly against the sleeves 60 and 80 when the steering shaft 30 is inserted all the way into the lumen 45 and is seated against shoulder 85 shown in FIG. 6. The end 43 may be attached to the controller 15 by means of a standard Luer lock 44.

The handle 20 shown in FIGS. 1 and 6 is generally cylindrical in shape and includes a forward section 90 (shown in dotted fashion in FIG. 1), a middle section 100, and a rear section 110. The forward section 90 has an outer diameter closely matching the inner diameter of the first sleeve 50, and is positioned within the sleeve 50 in a slidable fashion. The middle section 100 has a reduced outer diameter, and the rear section 110 has an outer diameter which is chosen for a comfortable grasp by the hand of the operator.

The sleeves 50, 60, and 80 and the three sections of the handle 20 all include central bores which are coaxially aligned for receiving a steering wire 120, as shown in FIG. 6. One end of the wire 120 is clamped in position relative to the handle 20 by means of a screw 130, shown in FIG. 1, which is threaded into a bore 140, shown in FIG. 6.

The steering wire 120 includes a distal end 150 which is flattened in the preferred embodiment such that it has a rectangular cross section, and extends into a distal end 160 of the shaft 30. A coiled spring or sleeve 170 defines a central lumen 180 within the steering shaft 30, in which lumen the steering wire 120 is positioned. A ferrule 190 is positioned within the shaft 30 immediately distal of, and abutting, the coiled spring 170. The ferrule 190 includes a central lumen 200, and two slots 210 and 220 (as shown in FIG. 29) which are disposed radially opposite one another, and together form a single transverse slot.

Figure 2:
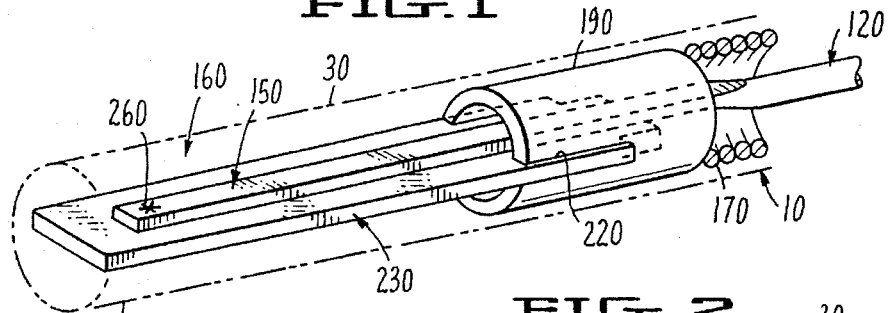
FIG. 2 is an enlarged perspective view of a portion of the mechanism of FIG. 1.
Figure 3:
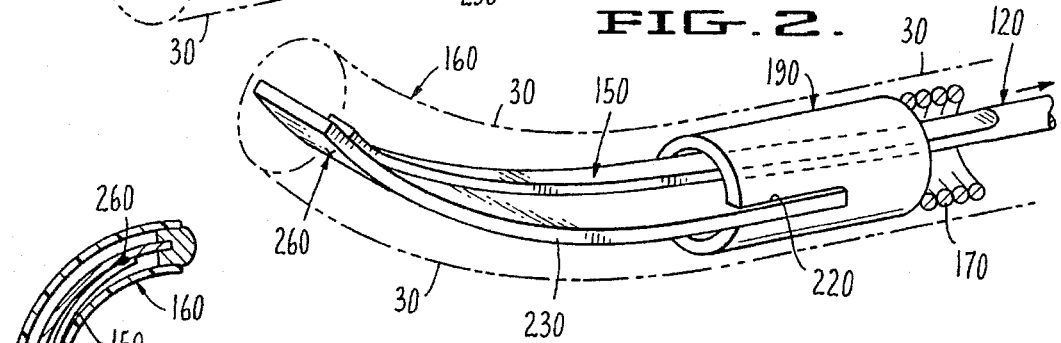
FIG. 3 is an enlarged perspective view similar to FIG. 2, showing a different position for the mechanism.

A flat, flexible lead spring 230 is positioned within the slots 210 and 220. The lead spring 230 includes a tongue 240 on its proximal end, which has a width closely matching the inner diameter of the ferrule 190. The lead spring 230 also includes a broader portion 250 with an outer diameter closely matching the outer diameter of the ferrule 190. Thus, when the lead spring 230 is positioned as shown in FIGS. 2 and 3, the tongue 240 (FIG. 29) is within the ferrule 190, and the proximal end of the broader portion 250 abuts the bottom ends of the slots 210 and 220. With the ferrule 190 and lead spring 230 in the position shown in FIG. 1, the distal end 150 of the steering wire 120 is welded or otherwise attached to the lead spring 230, such as at weld 260.

Figure 5:
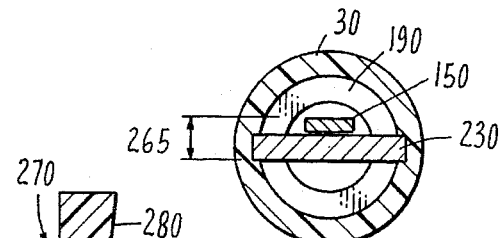
FIG. 5 is a sectional view taken along line 5—5 of FIG. 4.

As shown in FIG. 5, the ferrule 190 and the shaft 30 have inner diameters which are substantially greater than the combined thickness 265 of the distal end 150 of the steering wire 120 and the lead spring 230.

In an alternative embodiment, shown in FIG. 36, the ferrule 190 may be omitted, in which case the lead spring 230 is inserted into the coiled spring 170 in much the same fashion as into the ferrule 190, with the same dimensions applying to this embodiment. The lead spring 230 may be attached to the coiled spring 170 by adhesive, solder, welds, or the like.

Referring now to FIGS. 1 and 6, the middle section 100 of the handle 20 includes a transverse slot therethrough, into which a control wedge 270 is positioned. The wedge 270 includes a larger end 280 tapering towards a smaller end 290. The wedge 270 also includes a slot 300 extending most of its length, as shown in FIGS. 1 and 6. The wedge 270 is positioned such that the wire 120 passes through the slot 300, as shown in FIG. 6, in which position the slot 300 is generally parallel to the longitudinal axis of the handle 20, and also is parallel to the proximal end of the wire 120. The ends 280 and 290, which form the ends of the slot 300, prevent the wedge 270 from accidental removal.

When the wedge 270 is in the upper position shown in FIGS. 1 and 6, the distal end 160 of the shaft 30 has the configuration shown in FIG. 2. However, when the wedge 270 is pushed downward to the position shown in dotted fashion in FIGS. 1 and 6, this forces the first sleeve 50 forwardly relative to the handle 20, by increasing the distance therebetween. Alternatively speaking, the handle 20 is forced rearwardly relative to the sleeve 50, into the position shown in dotted fashion (at the extreme right end) in FIGS. 1 and 6. The proximal end of the wire 120, being affixed by the screw 130, is similarly moved towards the right from the point of view of FIG. 6, to the position shown in dotted fashion.

Figure 4:
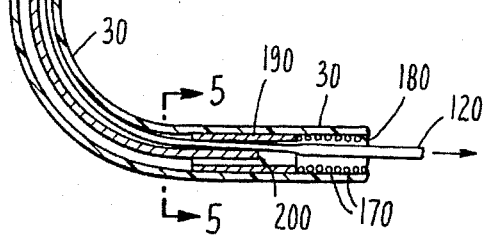
FIG. 4 is a sectional view of the mechanism of FIG. 1 in yet another position.

The wire 120 is thus pulled toward the right from the point of view of FIGS. 1–4 and 6, and thereby pulls the lead spring 230 at the weld 260, as shown in FIG. 3. This bends the lead spring 230 in the direction of the distal end 150 of the wire 120, thus bending the distal end 160 of the shaft 30, as shown in FIGS. 2 through 4.

It will be appreciated that, because of the relatively large inner diameters of the ferrule 190 and the shaft 30, lateral torque or leverage may be exerted by the distal end 150 on the lead spring 230, in order to effect bending of the distal end 160 of the shaft 30. Thus, by providing enough radial play to the distal end 150 of the wire 120 and the lead spring 230, sufficient torque for steering the distal end 160 may be assured. The amount of radial play may be determined empirically for a given application, but in most cases a minimum inner diameter of the lead spring 230 and the shaft 30 of approximately two to three times the combined thickness 165 shown in FIG. 5 will be sufficient to provide the necessary torque.

The materials for the wedge 270, the handle 20 and the sleeve 50 are chosen to provide sufficient friction, such that the wedge 270 maintains its position wherever it is located by the operator, so that the distal end 160 can be fixed in a variety of positions simply by repositioning the wedge 270. The wire 120 may be tightened by loosening the screw 130, pulling the wire 120 tight, and then retightening the screw 130, which results in a change in the frictional fit of the wedge 270. Access to the proximal end of the wire 120 may be had through an opening 310 in the rear section of the handle 130.

In the preferred embodiment, the lead spring 230 is affixed to the ferrule 190, and the ferrule 190 is in turn affixed to the coiled spring 170. This may be done by adhesive, welds or the like, and is especially useful in conjunction with a catheter which is to be emplaced permanently or for a long period of time within a patient. The ferrule may alternatively simply be abutted against the coiled spring 170, in which case the distal end 160 of the steering shaft is preferably formed from a heat shrink or other tightly fitting material to maintain the ferrule firmly in place.

In use, a physician will insert the catheter 40 into a patient, such as into the femoral vein, and will insert the shaft 30 into the lumen 45. By manipulating the distal end 160 as necessary and pushing on the handle 20, the physician can negotiate a path to the treatment site, such as the heart. The physician may, by operating the control wedge 270, steer past any junction, turn or obstacle which may be presented to the catheter simply by adjusting the control wedge such that the distal end 160 of the shaft 30, and hence also the distal end 48 of the catheter 40, takes on the necessary shape. Once a given obstacle or turn is negotiated by the end 160, it can then again be straightened out by operation of the wedge 270, or may be changed to a different shape as necessary. If, for instance, the physician encounters a turn of the vein towards the right, the wedge 270 is pushed downward as shown in FIG. 1, such that the distal end 160 takes on the position shown in dotted fashion. If the vein then takes a turn to the left, the physician straightens out the distal end 160, rotates the handle 20 such that the distal end 160 rotates the necessary amount (such as 180°), and then again operates the wedge 270 to manipulate the distal end 160 around the left turn. In this way, complete control over steering and emplacement of the catheter 40 is achieved.

FIGS. 7–10 show an alternative embodiment, wherein left and right turns may be negotiated without rotation of the apparatus. The steering mechanism 315 shown in FIG. 7 includes a flexible steering shaft 320 having a proximal end 330 and a distal end 340 and may be identical to the shaft 30 shown in FIG. 1. As shown in FIG. 8, carried within the distal end 340 are a lead spring 350 and two steering wires 360 and 370. The steering wires 360 and 370 are preferably rounded towards their proximal ends, and flattened towards their distal ends, as with the steering wire 120 shown in FIG. 1. The steering wires 360 and 370 are attached to the distal end of the lead string 350 by solder, adhesive, spot welds or the like, such as at welds 380 and 390. For minimizing friction, the steering wires 360 and 370 (and the steering wires of any of the embodiments described herein) are preferably coated with TEFLON.

The lead spring 350, which may be identical to the lead spring 230 shown in FIG. 2, is seated in a ferrule 400, which is shown in FIG. 8 and may be identical to the ferrule 190 shown in FIG. 2. Thus, the configuration of the distal end 340 of the shaft 320 shown in FIG. 8 is essentially identical to the distal end 160 of the shaft 30 shown in FIG. 2, except that an additional steering wire is attached to the lead spring 350. The mechanism 315 may be used in the same applications as the mechanism 10.

FIGS. 25–28 show further detail of the distal tip of a steering shaft of the embodiment of FIGS. 7–10, with FIGS. 26, 27 and 28 showing cross-sectional views at the regions indicated in FIG. 25 along the length of the shaft 320. The numerals appearing in FIGS. 25–28 are the same as those in FIGS. 7 and 8, but the details of these figures may be employed in any of the other embodiments described herein which utilize two steering wires.

In FIGS. 25–28, the shaft 320 is shown as used in conjunction with the catheter 40 shown in FIG. 35. Preferably, the catheter 40 includes a standard braided or other torquable material, and the shaft 320 is adhered to the interior of the catheter 40 by adhesive means such as glue 405 shown in FIGS. 25 and 27. With this configuration, torque on the proximal end of the catheter 40 will be transmitted to its distal end, and via the glue 405 will be transmitted to the shaft 320, thus allowing for turning of the distal end 340. Alternatively, and especially in embodiments wherein no catheter is used, the shaft 320 may be made of a torquable material.

Distal end 340 of the shaft 320 receives the lead spring 350 and the steering wires 360 and 370, as shown in FIG. 25. The rounded or circular proximal ends of the steering wires 360 and 370 are positioned within a coiled sleeve 375, as shown in FIG. 28. The coiled sleeve 375 may be a conventional metal coil such as those used in medical catheters to provide longitudinal stiffness but lateral flexibility. The steering wires 360 and 370 are flattened into a rectangular shape in the region near the lead spring 350.

In the preferred embodiment, the steering wires 360 and 370 are attached at several places to the lead spring 350, such as at the three spot welds 380 and the three spot welds 390, respectively, shown in FIG. 25. The distal end 340 may be a heat-shrink material which, once the elements of the steering mechanism are assembled, is heated to reduce its diameter relative to the main body of the shaft 320, thus tapering the tip in the region of the spot welds 380 and 390, as shown in FIG. 25. When spot welds are used to attach the steering wires to the lead spring, the use of heat-shrink is particularly advantageous in applying pressure to the welded region to prevent separation. When solder is used, this is not as important a consideration.

FIGS. 30–32 show an alternative embodiment of the distal end of the invention, wherein the proximal portions of the steering wires 360 and 370 are of non-circular cross section, such as the rectangular cross section shown in this embodiment. The steering wires 360 and 370 may be further flattened, as shown in FIG. 31, in the region of the lead spring 350, thus providing greater clearance between the combined thickness 385 of the steering wires 360 and 370 and the lead spring 350, on the one hand, and the inner diameters of the ferrule 400 and the shaft 320, on the other hand. As discussed above relative to FIGS. 1–5 (and as shown in FIG. 5), this clearance allows greater torque to be placed upon the distal tip of the steering shaft when the physician turns the distal tip by placing tension on the steering wires.

Referring again to FIGS. 7–10, it will be seen that the configuration shown in FIGS. 25–28 (or 30–32) allows either left or right turns to be effected by pulling on the wire 360 or the wire 370, as shown in dotted fashion for the distal end 340 in FIG. 7. FIG. 8 shows the configuration of the distal end 340 of the shaft 320 for a right turn, wherein rearward tension is placed on the steering wire 370 (represented by the right-facing arrow), and a forward force is simultaneously applied to the steering wire 360 (as represented by the left-facing arrow). The forward force to the wire 360 occurs both because of the push given to the wire 360 by the clockwise rotation of the spindle 450 (which is described in greater detail below), and because of the pull exerted by the wire 370 via the welds 390, the lead spring 350, and the welds 380. When the spindle 450 is rotated counterclockwise, force is placed on the steering wires 360 and 370 in directions opposite to the arrows shown in FIG. 8, thus bending the distal end 340 to the left, as shown in dotted fashion.

In order to provide such tension to the steering wires, a controller 410 is provided, as shown in FIGS. 7, 9 and 10. The controller 410 includes a housing 420 which receives the proximal end 330 of the shaft 320. Attached to the housing 420 is a coupling 430 which has a central bore 440 (shown in dotted fashion in FIG. 9) which is substantially coaxial with the lumen of the shaft 320.

The guide wires 360 and 370 pass through the bore 440, and are attached as shown in FIGS. 9 and 10 to a spindle 450. The preferred means of attachment is by insertion through a bore 460 in the spindle 450, and the proximal tips 470 and 480 of the steering wires 360 and 370, respectively, are bent to prevent retraction through the bore 460. The wires are chosen to be stiff enough that they will retain the bent shape at their proximal tips, and will not retract from the bore 460. Optionally, a taper pin 485 may also be used, being driven between the ends 470 and 480 into a frictional fit in a flared portion 465 of the bore 460, thus preventing the proximal tips 470 and 480 from accidental withdrawal.

The housing 420 includes a central passage 490, through which the steering wires 360 and 370 pass, and may include a threaded portion 500 in which an adjustable, threaded tension adjusting screw or bolt 510 is positioned. The tension bolt 510 includes a central bore 520, as shown in FIG. 10, and a knurled knob 530 for adjustment by hand. As shown in FIG. 7, the knob 530 may be accessed by the operator of the controller 410 at any time, without disassembling the steering mechanism. The knob 530 is turned to adjust tension on the steering wires 360 and 370, and to adjust the amount of play in the lead spring 350, as described in greater detail below.

The spindle 450 is mounted on an axis which is preferably transverse to a longitudinal axis of the housing 420, and is rotatable by means of a steering handle 540, which is connected to the spindle 450 by a shaft 550. The spindle 450 and associated steering apparatus are affixed to the housing by means of a plate 552 which is mounted to the housing 420 by means of screws or bolts 554.

The shaft 550 includes a threaded bottom end 560, onto which a tightening knob 570 is threaded. A washer 580 is preferably positioned between the knob 570 and the housing 420, and a resilient O-ring 590 is positioned adjacent the washer 580. Between the O-ring 590 and the knob 570 is positioned another washer 600.

The washers 580 and 600 and the O-ring 590 are all coaxial with and surrounding the threaded portion 560 of the shaft 550. Thus, when the knob 570 is rotated such that it is tightened (i.e., moved closer to the housing 420), the increased friction between the knob 570, the washers 580 and 600, the O-ring 590 and the housing 420 inhibits the shaft 550 from turning, thereby maintaining the handle 540 in any position set by the operator of the steering mechanism. The resiliency of the O-ring 590 allows the operator to adjust the friction by means of the knob 570 such that the handle 540 may be relatively easily rotated by pushing with the fingers, and yet such that the distal end 340 will not spring back to the straightened shape shown in FIG. 7 (which would cause the handle 542 spring back to the central position shown in FIG. 7) when the operator releases the handle 540. Alternatively, the knob 570 may be loosened such that whenever the operator manipulates the handle 540, and then releases the handle, the distal end 340 is allowed to straighten out—which it will do because of the tension of one or the other of the steering wires, such as the tension due to the steering wire 360 in the position shown in FIG. 8.

In order to increase the tension in the steering wires 360 and 370 and decrease the rotational play in the handle 540, the knob 530 is rotated such that it moves to the left from the point of view of FIG. 10 (which will be a counterclockwise rotation for right-hand threads), thereby exerting force on the proximal end 330 of the coiled sleeve 375 (the force being towards the left in FIG. 10). The sleeve 330 is longitudinally relatively rigid, and thus the force on its proximal end is transmitted to its distal end, where it is exerted in turn on the ferrule 400, and thence onto the lead spring 350. The force on the lead spring 350 is transmitted to the steering wires 360 and 370 via the welds 380 and 390. Thus, any longitudinal play in the system is reduced or eliminated by the counterclockwise rotation of the tension bolt 510, which results in greater responsiveness in the rotational control of the lead spring 350 by means of the steering handle 540.

Conversely, tension on the steering wires is reduced, and greater play is given to the steering function, by rotating the knob 530 such that it moves towards the right from the point of view of FIG. 10.

The embodiment of FIGS. 7–10, therefore, allows the operator of the steering mechanism to manipulate the catheter into whatever position desired, accommodating both left and right turns through the passages encountered in the body. At most, the distal end 340 of the shaft 320 will need to be rotated 90° to accommodate all possible twists and turns that might be encountered in the body. The controller 410 may be manipulated entirely with one hand, including both operating the handle 540 to position the distal end 340 into the right and left turn configurations shown in dotted fashion in FIG. 7, and also including axial rotations of the distal end 340 should those become necessary.

Figure 11:
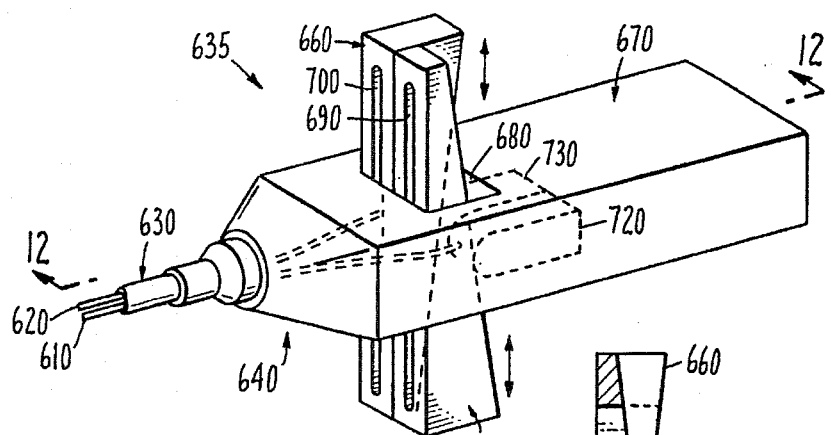
FIG. 11 is a perspective view of another embodiment of the invention.
Figure 12:
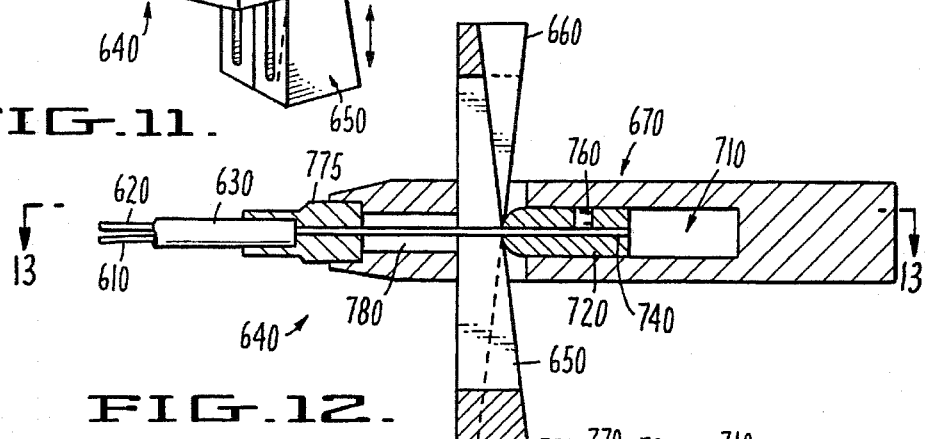
FIG. 12 is a sectional view taken along line 12—12 of FIG. 11.
Figure 13:
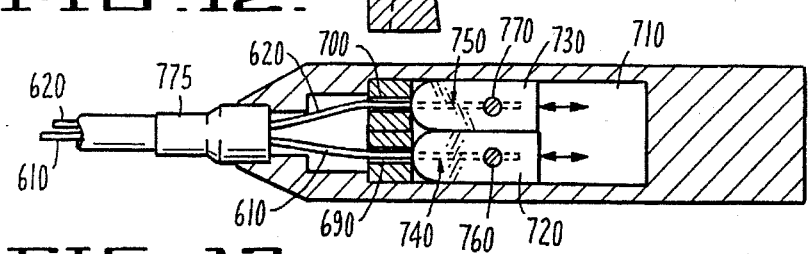
FIG. 13 is a sectional view taken along line 13—13 of FIG. 12.

FIGS. 11–13 show an alternative embodiment of the invention comprising a steering mechanism 635 which incorporates two steering wires 610 and 620 which extend through a flexible steering shaft 630. The portion of the mechanism extending to the left from the point of view of FIG. 11 may be identical to the embodiment shown in FIGS. 7 and 8. The steering mechanism 635 of FIGS. 11–13 includes a controller 640 which constitutes an alternative to the controller 410 shown in FIGS. 7, 9 and 10.

The controller 640 includes a left control wedge 650 and a right control wedge 660 mounted in a housing 670. The housing 670 includes an opening 680 in which the control wedges 650 and 660 are positioned as shown in FIGS. 11 and 12, with control wedge 650 being tapered upwardly, and control wedge 660 being tapered downwardly. The wedges 650 and 660 may be identical, except that they are carried in opposite directions in the housing 670.

Control wedge 650 includes a slot 690, and control wedge 660 includes a slot 700. These slots terminate at the upper and lower ends of the control wedges, as shown in FIG. 11.

The housing 670 includes a cavity 710 in which a left control block 720 and a right control block 730 are positioned, such that they may slide to the left and right from the point of view of FIGS. 11–13 (as shown by the double arrows in FIG. 13). The left control block 720 includes a bore 740, and the right control block 730 includes a bore 750, into which the extreme proximal ends of the steering wires 610 and 620 extend, as shown in FIG. 13. Screws 760 and 770 are provided, as shown in FIGS. 12 and 13, and are threaded into the control blocks 720 and 730 for clamping down the proximal ends of the steering wires 610 and 620.

As shown in FIGS. 11–13, the steering wires 610 and 620 extend from the steering shaft 630 through a wire retainer 775 and through a bore 780 in the distal end of the housing 670, through the slots 690 and 700, and thence into the bores 740 and 750, where they are held in place by the screws 760 and 770. Thus, if left control block 720 is forced to the right from the point of view of FIG. 13, then tension is placed on steering wire 610, thereby turning the distal tip of the steering shaft 630 (and also the distal tip of the catheter in which the shaft is positioned) to the left (as shown in dotted fashion in FIG. 7). Likewise, if right control block 730 is forced to the right, tension is placed on the steering wire 620, forcing the distal tip of the steering shaft 630 (and the distal tip of the catheter) to the right. Again, only one hand is needed to operate the controller 640, and at most a 90° turn of the distal tip of the steering shaft 630 will be required to negotiate all twists and turns within the passages in the body of a patient. As will be discussed in further detail below, the controller 640 of FIGS. 11–13 has particular advantages when used with a distal tip of the configuration shown in FIGS. 21 and 22.

Figure 14:
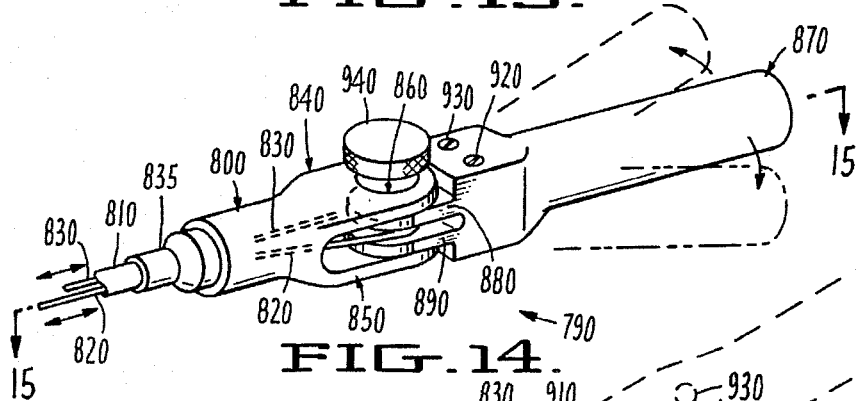
FIG. 14 is a perspective view of yet another embodiment of the invention.
Figure 15:
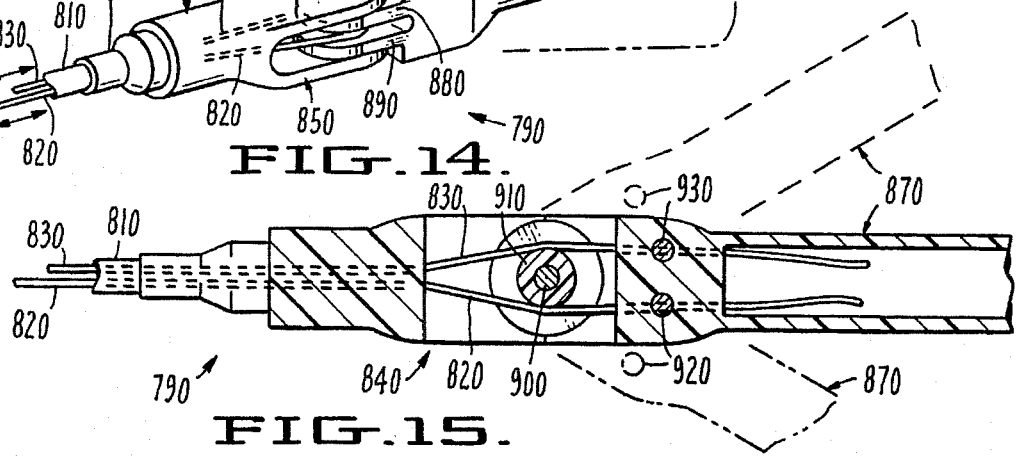
FIG. 15 is a sectional view taken along line 15—15 of FIG. 14.

FIGS. 14 and 15 show a controller 790 of the invention which is an alternative to the controller 640 of the embodiment of the invention shown in FIGS. 11–13. The controller 790 forms a part of a steering mechanism having a distal end which may be identical to the embodiment of FIGS. 7 and 8, or may, as described below, be like the embodiment shown in FIGS. 21 and 22.

The controller 790 includes a housing 800 which receives a steering shaft 810, and also receives steering wires 820 and 830 through a wire retainer 835.

The housing 800 includes flanges 840 and 850 with coaxial bores (such as bore 860) therethrough, with bore 860 being formed through the flange 840 and another bore (not separately shown) being formed through flange 850. The bores have an axis which is substantially at right angles to a longitudinal axis of the housing 800 and the steering shaft 810. The controller 790 includes a handle 870 having forwardly disposed flanges 880 and 890 which include transverse bores therethrough (not separately shown) which are coaxial with the bores through the flanges 840 and 850. Extending through the bores in the flanges 840, 850, 880 and 890 is a shaft 900 (shown in FIG. 15). The shaft includes an annular bearing 910. As shown in FIG. 15, the steering wires 820 and 830 are disposed on opposite sides of the bearing 910 and are affixed to the handle 870 by means of screws 920 and 930. A tightening knob 940 (shown in FIG. 14) is coupled to the shaft 900, preferably by threading onto an end thereof, and is used to adjust friction in the same manner as the knob 570 shown in FIG. 9.

When the handle 870 is pulled to the left, as shown in dotted fashion in the lower portion of FIG. 15, rearward tension is placed on the steering wire 830 and a forward force is exerted on the steering wire 820. This causes the distal tip of the steering shaft to bend to the right, as shown in dotted fashion on the upper side of the steering shaft 320 in FIG. 7. Conversely, when the handle 870 is pushed to the right with respect to the housing 840, as shown in dotted fashion in the upper portion of FIG. 15, rearward tension is placed on the steering wire 820 and a forward force is exerted on the steering wire 830, causing the distal tip of the steering shaft to bend to the left, as shown in dotted fashion on the lower side of the steering shaft 320 in FIG. 7. As with the embodiment of FIG. 9, the knob 570 may be tightened such that the handle 870 will maintain whatever position it is placed in, or it may be loosened to allow much freer play to the handle 870.

Figure 16:
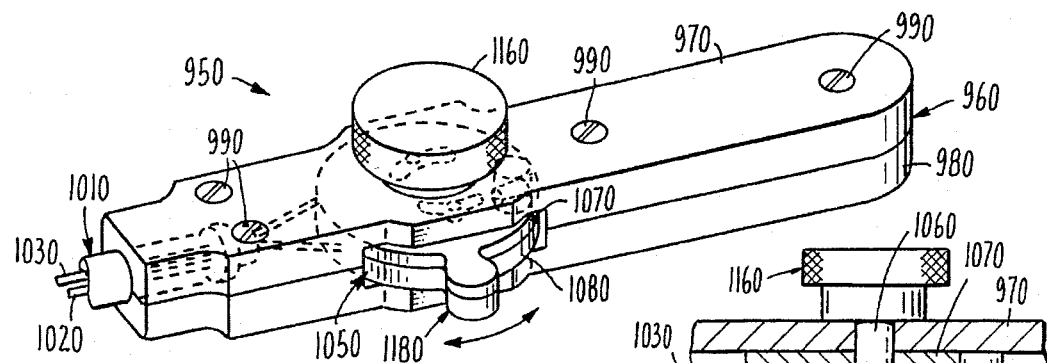
FIG. 16 is a perspective view, partially cut away, of another embodiment of the invention.
Figures 17A, 17B:
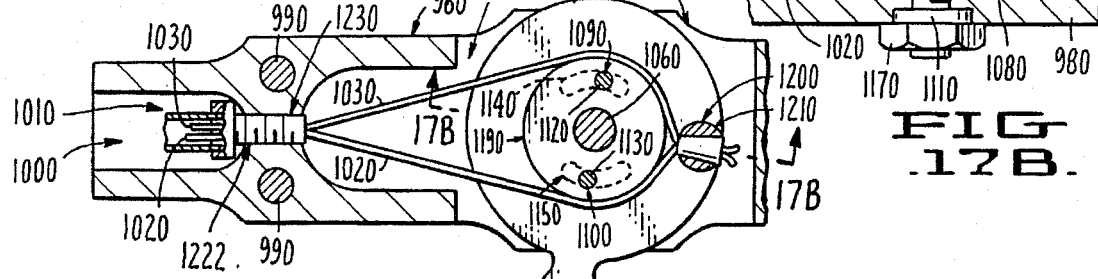
FIG. 17A is a top view, partly cut away, of the embodiment of FIG. 16.
FIG. 17B is a sectional view taken along line 17B—17B of FIG. 17A.

FIGS. 16, 17A and 17B show another embodiment of the controller of the invention. The controller 950 includes a housing 960 having an upper half 970 and a lower half 980. These halves are held together by screws 990. The housing 960 includes a bore 1000 in its distal end, for receiving a proximal end of a steering shaft 1010, in which steering wires 1020 and 1030 are positioned. The portion of the steering shaft 1010 and steering wires 1020 and 1030 to the left of FIG. 16 may be identical to the distal portion of the steering shaft shown in FIGS. 7 and 8.

The housing 960 includes a cavity 1040 defined between the two halves 970 and 980, in which a disk 1050 is rotatably mounted, with its axis of rotation defined by a shaft 1060 disposed substantially at right angles to a longitudinal axis of the housing 960. The disk 1050 includes an upper half 1070 and a lower half 1080, into which are inserted dowels or pins 1090 and 1100. The pins 1090 and 1100 are received by coaxial bores (not separately shown) in the upper and lower halves 1070 and 1080, respectively. The pins 1090 and 1100 include heads or tips 1120 and 1130, which protrude above the upper half 1070 of the disk 1050. Corresponding arcuate slots 1140 and 1150 are provided in the lower surface of the upper half 970 of the housing 960, thus limiting the rotational travel of the disk 1050.

The steering wires 1020 and 1030 are clamped between the upper half 1070 and the lower half 1080. Attached to the upper end of the shaft 1060 is a knurled knob 1160, onto the lower end of which a nut 1170 is threaded, as shown in FIG. 17B. The nut 1170 may include a press-nut portion 1110, which has a non-circular cross-section and is press-fit into the lower half 980 of the housing 960, as shown in FIG. 17B. This allows the nut 1170 to be tightened without the use of a wrench.

The knob 1160 is used to adjust the friction imparted by the housing 960 to the disk 1050, in similar fashion to the knob 940 of the controller 790 shown in FIG. 14.

A tab 1180 is formed on a side of the disk 1050, by protruding portions of the upper and lower halves 1070 and 1080. The tab 1180 forms a grip for the thumb of the operator. An additional tab (not separately shown) may be formed diametrically opposite the tab 1180.

The extreme proximal ends of the steering wires 1020 and 1030 are clamped in place around a bearing 1190 by means of a standard clamp 1200, which may include a conventional taper pin (like the taper pin 485 shown in FIG. 10). The clamp 1200 is tightly received in a flared indentation 1210 formed in one or both of the halves 970 and 980 of the disk 960.

Thus, as the tab 1180 is pushed clockwise from the point of view of FIG. 17A, rearward tension is placed on the steering wire 1030, and a forward force is exerted on the steering wire 1020. The distal tip of the steering shaft 1010 is thus turned to the right, as described previously with respect to the steering shaft 320 shown in FIG. 7. Pushing on the tab 1180 counterclockwise from the point of view of FIG. 17A likewise turns the distal tip of the steering shaft 1010 to the left.

A tightening screw 1220 is preferably threaded into a bore 1230 in the housing 960, by which the tension on the steering wires 1020 and 1030 may be adjusted by screwing the tightening screw 1220 into or out of the bore 1230. This operates in the same fashion as the threaded bolt 510 shown in FIGS. 9 and 10.

Figure 18:
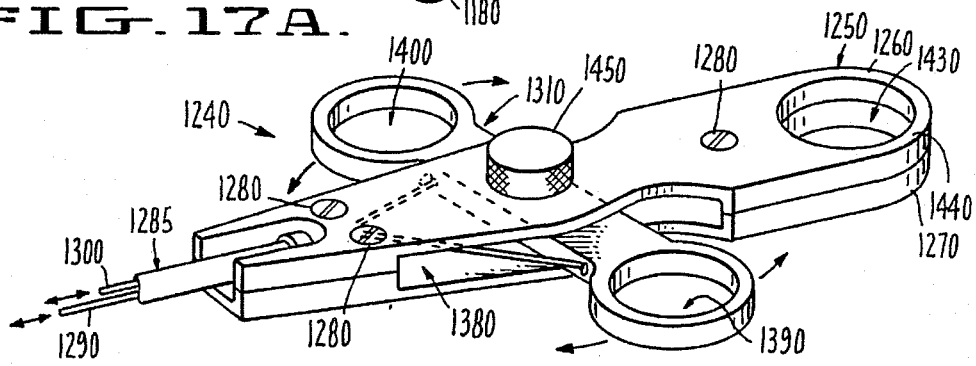
FIG. 18 is a perspective view of another embodiment of the invention.
Figure 19:
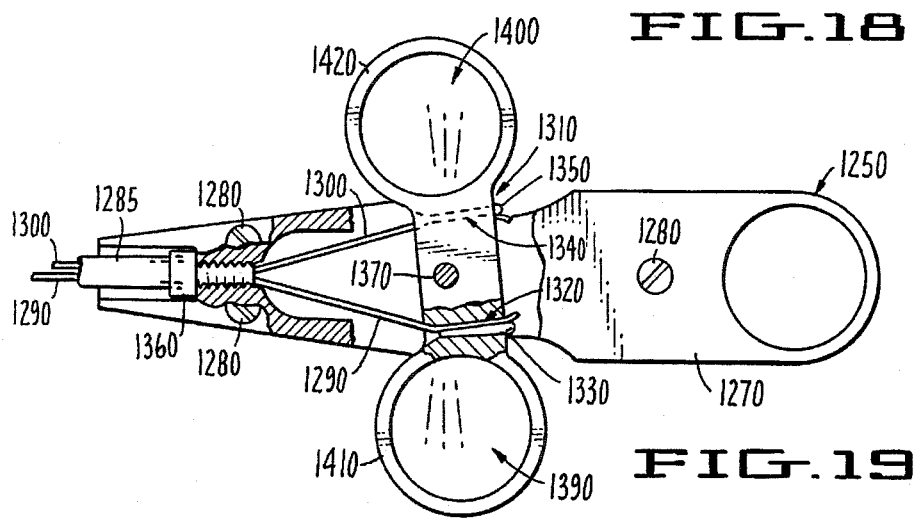
FIG. 19 is a top view of the embodiment of FIG. 18.

Another embodiment of the invention is shown in FIGS. 18 and 19, depicting a controller 1240 which is an alternative to the controllers described above. The controller 1240 includes a housing 1250, including an upper half 1260 and a lower half 1270, which are held together by means of screws 1280. The housing receives a steering shaft 1285, in which are disposed steering wires 1290 and 1300. The distal portion of the steering shaft 1285 may be identical to the distal portion of the shaft 320 shown in FIG. 7.

The steering wires 1290 and 1300 are attached to a rotator 1310, as shown in FIG. 19. Any conventional attachment method may be used, but in the embodiment shown the extreme proximal end of the steering wire 1290 passes through a tapered slot 1320 formed in the rotator 1310, and a wedge or taper pin 1330 is tightly fitted into the slot 1320, thus preventing the steering wire 1290 from slipping out of the slot. Likewise, the steering wire 1300 is positioned in a slot 1340 and is maintained in position by a wedge or taper pin 1350. Tension on the steering wires 1290 and 1300 may be adjusted by means of a bolt 1360, just as with the tightening screw 1220 shown in FIG. 17A.

The rotator 1310 is rotatably mounted on a shaft 1370 which is substantially at right angles to a longitudinal axis of the housing 1250 and the longitudinal axis of the steering shaft 1285. A slot 1380 is formed between the upper and lower housing halves 1260 and 1270, as shown in FIG. 18. Thus, the operator of the mechanism may turn the distal end of the steering shaft 1285 to the left or right by rotating the rotator 1310 counterclockwise or clockwise, respectively. Finger holes 1390 and 1400 are formed by circular portions 1410 and 1420, which are in the preferred embodiment integral with the rotator 1310. This provides ease of operation of the controller 1240. Likewise, a finger hole or thumb hole 1430 is formed by a circular portion 1440 formed in the housing 1250.

The rotator 1310 is operated in essentially the same fashion as the disk 1050 shown in FIG. 16, but provides a different type of hand hold for the physician. A tightening knob 1450 is provided to adjust the friction on the rotator 1310, just as with the knurled knob 1160 of the embodiment of FIG. 16.

FIGS. 20–24 show an alternative embodiment of the invention, including a steering mechanism 1460 including steering wires 1470 and 1480, which terminate in distal tips 1490 and 1500, respectively. The steering mechanism 1460 includes a housing 1510, and shafts 1520 and 1530 which are transversely, rotatably mounted.

Carried on the upper end of shaft 1520 is a disk 1560 having an arcuate groove 1570 around its circumference. The disk 1560 is attached in a non-rotatable fashion to the shaft 1520. Mounted in the housing 1510 is a stop 1580, for limiting the rotational motion of the disks 1560 and hence of the shaft 1520, with the limit of rotation being determined by the arc length of the groove 1570. The shaft 1520 is rotated by turning the disk 1560.

Similarly, a disk 1590 is rigidly attached to the shaft 1530, and includes an arcuate groove 1600 around its perimeter. Another stop 1610 is mounted in the housing 1510, to limit the rotational motion of the disk 1590 and hence of the shaft 1530.

Figure 24:
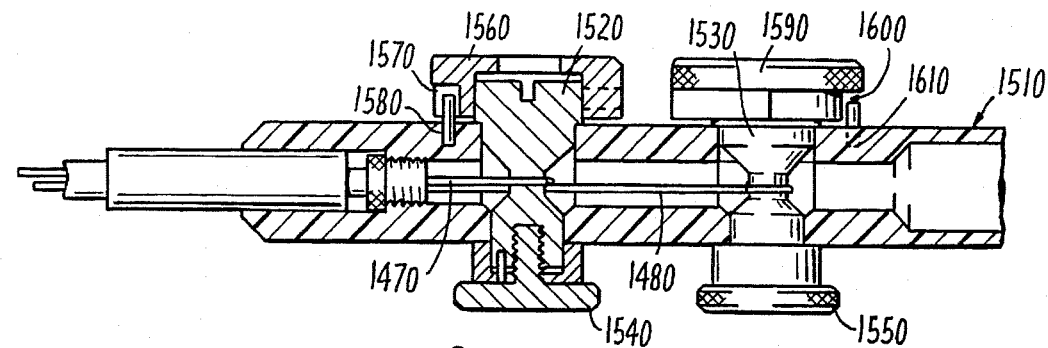
FIG. 24 is a sectional view taken along line 24—24 of FIG. 23.

Knobs 1540 and 1550 are threaded onto the shafts 1520 and 1530, as shown in FIG. 24, and provide rotational friction to the disks 1560 and 1590, respectively, in the same manner as the knob 570 shown in the embodiment of FIG. 7.

Figure 23:
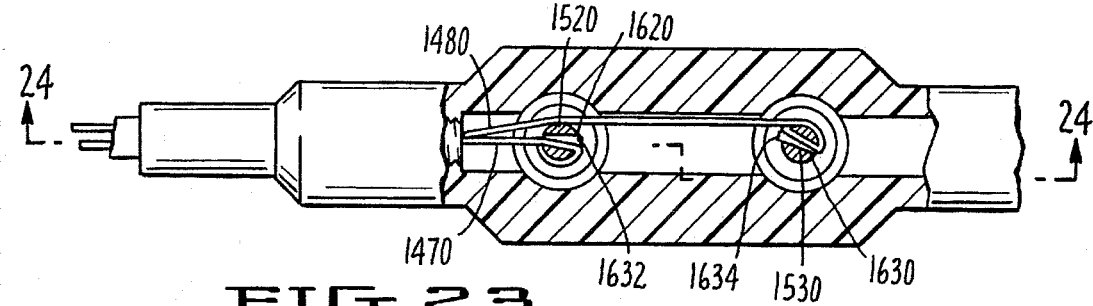
FIG. 23 is a top view, partially cut away, of the embodiment of FIG. 20.

As shown in FIG. 23, the steering wire 1470 is attached to the shaft 1520 by passing the extreme proximal end thereof through a bore 1620 formed in the shaft 1520, and by fixing the proximal tip so that the steering wire 1470 cannot slip relative to the bore 1620. Similarly, steering wire 1480 is attached to the shaft 1530 through a bore 1630.

Affixation of each of the steering wires to the respective shafts may be accomplished by any standard means, such as by wrapping the steering wire around itself, or by welds, adhesives, clamps or the like. In a preferred embodiment, the steering wires 1470 and 1480 are attached to the shafts 1520 and 1530, respectively, by means of conventional taper pins 1632 and 1634, in a friction fit to prevent the wires 1470 and 1480 from accidentally coming loose.

In the embodiment of FIGS. 20–24, the steering wire 1470 is attached to the extreme distal tip of a lead spring 1640 carried within a steering shaft 1650. The lead spring is positioned within a slot of a ferrule 1660. The configuration of the lead spring 1640, the ferrule 1660, and the attachment of the steering wire 1470 to the lead spring 1640 may be identical to the configuration of lead spring 350, ferrule 400, and steering wire 360 shown in FIG. 8. The lead spring 1640 is held in place relative to the steering shaft 1650 by means of an adhesive 1670. The adhesive 1670 may include an electrically conductive material, if the steering shaft 1650 is to be utilized in an embodiment wherein an electrode is desired at the tip of the steering shaft.

Figure 21:
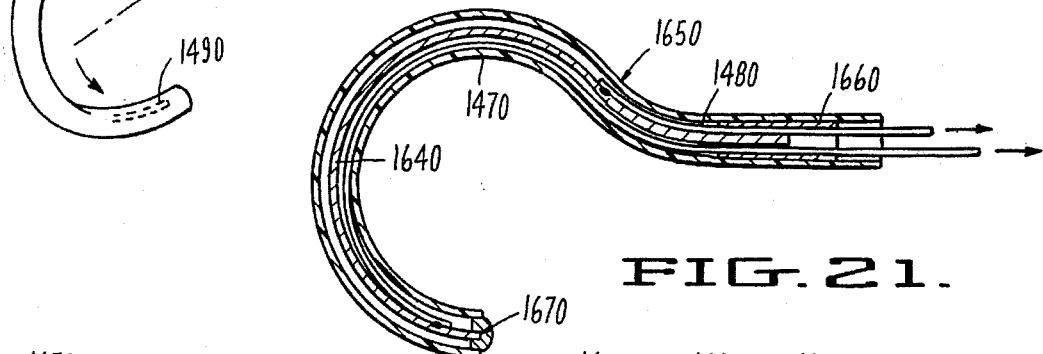
FIG. 21 is a sectional view of the distal end of the embodiment of FIG. 20.
Figure 22:
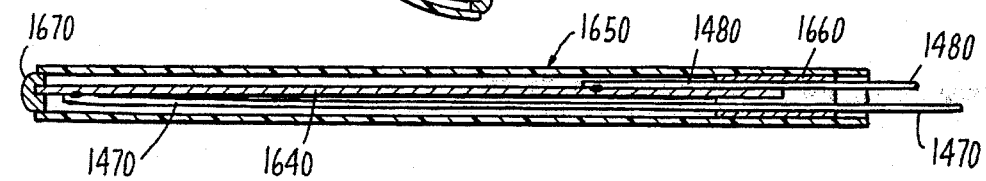
FIG. 22 is a sectional view like that of FIG. 21, in a straightened position.

In this embodiment, the steering wire 1480 is attached at its distal tip to the lead spring 1640 at a point somewhat removed from the distal tip thereof, as shown in FIGS. 21 and 22. With this configuration, rotation of the shaft 1520 so as to place tension on the steering wire 1470 will cause the extreme distal tip of the steering shaft 1650 to turn to the left, while placing tension on the steering wire 1480 (by rotating the shaft 1530) will cause the steering shaft 1650 to turn to the right at the point of attachment of the steering wire 1480 to the lead spring 1640. Such a configuration is shown in FIG. 21.

This embodiment has several advantages. For instance, tortuous paths may be negotiated by the tip of the steering shaft 1650 by operation of the knobs 1560 and 1590 while the physician views on a fluoroscope. Also, if the catheter (such as catheter 40 shown in FIG. 35) is to be positioned in a vessel which is complicated in shape, the configuration of FIG. 21, or variations thereon, may be the only way to position the distal tip of the steering shaft 1650 without placing too much stress on internal body structures. Another advantage is that the extreme distal tip of the steering shaft 1650 may be placed in position within the patient, and tension may then be taken off of the steering wire 1470, so that the distal tip of the steering shaft 1650 is free to flex, limited only by the flexibility of the lead spring 1640. However, at the same time, a bend may be retained in the portion of the steering shaft 1650 adjacent the attachment of the steering wire 1480 to the lead spring 1640, which is of particular importance where the catheter must make a turn very near the final emplacement point of the distal tip thereof, such as in the human heart.

Figure 20:
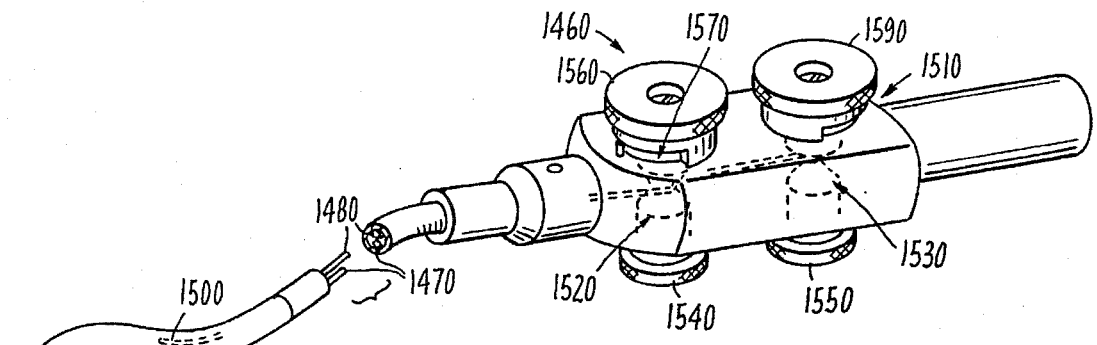
FIG. 20 is a perspective view of another embodiment of the invention.

Because the knobs 1560 and 1590 are operable independently of one another, the embodiment of FIG. 20 may take the hook-shaped configuration shown in FIGS. 20 and 21. However, the offset attachment of the steering wires 1470 and 1480 shown in FIG. 21 may also be used with other embodiments of the invention herein, indeed wherever two steering wires are used, such as in the embodiments of FIGS. 7, 11, 13, 16, and 18. In the embodiments where the steering wires are not independently operable, the hook-shaped configuration of FIG. 21 is not achieved. However, flexibility in the guiding of the distal tip of the steering shaft is in each case provided, by allowing bends in the distal tip of the steering shaft to be made at different points along its length, such as at its extreme distal tip and somewhat further back thereof.. This provides an extra measure of flexibility over the design of FIG. 1.

Shapes other than the hook shape of FIG. 21 may be achieved with different locations of attachment of the steering wires to the lead spring. Also, more than two steering wires may be used, if desired, with the various embodiments described herein. For instance, it may be desirable to have two offset steering wires attached to one side of the lead spring and one steering wire attached to the other side of the lead spring, to accommodate a particular configuration of emplacement. Alternatively, it may be useful for particular applications to attach steering wires at different angles circumferentially around a lead spring (which may be oval or polygonal in cross section). Other variations on the number, attachment and positioning of the steering wires may be made, and the shapes of the steering wires and the lead spring may be adapted accordingly.

Further flexibility may be accomplished by the present invention utilizing the configurations of FIGS. 33 and 34. In this embodiment, a steering shaft 1680 includes a distal tip 1690, having regions 1700 and 1710 of enlarged diameter. A lead spring 1720 is positioned within the distal tip 1690, and has its proximal end mounted in a ferrule 1730. A steering wire 1740 is attached at its extreme distal tip to the lead spring 1720, such as at weld 1750. The configuration of the lead spring 1720, ferrule 1730, and steering wire 1740 may be essentially identical to the embodiment of FIG. 2.

When tension is placed on the steering wire 1730, it will be seen from FIG. 34 that the distal end 1690 of the steering shaft 1680 takes sharp bends in two places, namely in the regions 1700 and 1710. This allows the physician greater flexibility in maneuvering around particular obstructions and negotiating difficult pathways through a vessel in the patient3 s body. Both this embodiment and the embodiment of FIGS. 20–24 may be carefully constructed such that the distance between bends and the resultant radii of curvature are adapted for a particular medical or other applications. For instance, the embodiments of FIGS. 20–24 or 33–34 may be custom designed for emplacement within the left ventricle of the heart, given the known shape of the heart. Other adaptations are easily accomplished with these designs.

What is claimed is:

1. A steering mechanism comprising:
   a steering shaft having a proximal end and a distal end and a lumen therethrough;
   a ferrule mounted in the steering shaft and having a distal end that terminates within the steering shaft short of the distal end of the steering shaft, the distal end of the steering shaft being free of any portion of the ferrule;
   a lead spring attached to the ferrule, the lead spring having an axis and a bendable portion extending outside the distal end of the ferrule but still within the distal end of the steering shaft that is free of any portion of the ferrule for bending the distal end of the steering shaft in response to an applied force relative to the ferrule;
   a steering wire extending through the lumen, said steering wire having a first end attached to the lead spring at a first location outside the distal end of the ferrule and having a second end exiting the proximal end; and
   a controller positioned at the proximal end and attached to the second end of said steering wire for placing tension on said steering wire, for applying force to said steering wire to bend the distal end of the steering shaft toward said tensed steering wire.

2. The steering mechanism of claim 1, wherein the controller includes:
   a housing connected to the steering shaft;
   a shaft rotatably mounted in the housing, with the second end of said steering wire being attached to the shaft;
   means attached to the shaft for rotating the shaft, for placing tension on the steering wire.

3. The steering mechanism of claim 1, wherein the controller includes
   a housing connected to the steering shaft;
   control element means mounted in the housing, with the second end of said steering wire being attached to the control element means, the control element means being operable for placing tension on said steering wire; and
   a manually movable element accessible outside the housing and attached to the control element means for placing tension on said steering wire by operation of the control element means.

4. A steerable catheter including
   a handle,
   a steering shaft having a proximal end attached to the handle and a distal end and a lumen therethrough;
   a ferrule mounted in the steering shaft and having a distal end that terminates within the steering shaft short of the distal end of the steering shaft, the distal end of the steering shaft being free of any portion of the ferrule;
   a lead spring attached to the ferrule, the lead spring having an axis and a bendable portion extending outside the distal end of the ferrule but still within the distal end of the steering shaft that is free of any portion of the ferrule for bending the distal end of the steering shaft in response to an applied force relative to the ferrule;
   a steering wire extending through the lumen, said steering wire having a first end attached to the lead spring at a location outside the distal end of the ferrule and having a second end exiting the proximal end; and
   a controller positioned on the handle and attached to the second end of said steering wire, for placing tension on said steering wire for applying force to said steering wire to bend the distal end of the steering shaft toward said tensed steering wire.

5. A steering mechanism, including:
   a steering shaft having a proximal end and a distal end and a lumen therethrough;
   a ferrule mounted in the steering shaft;
   a lead spring attached to the ferrule, the lead spring being positioned within the distal end and fixed in place relative to the ferrule;
   a steering wire extending through the lumen said steering wire having a first end attached to the lead spring and having a second end exiting the proximal end;
   a controller positioned at the proximal end and attached to the second end of said steering wire for placing tension on said steering wire for causing the distal end to bend toward said tensed steering wire, the controller comprising
   a housing connected to the steering shaft;
   a shaft rotatably mounted in the housing, with the second end of said steering wire being attached to the shaft; and
   means attached to the shaft for rotating the shaft, for placing tension on said steering wire.

6. A steering mechanism comprising:
   a steering shaft having a proximal end and a distal end and a lumen therethrough;
   a ferrule mounted in the steering shaft and having a distal end that terminates within the steering shaft short of the distal end of the steering shaft;
   a lead spring attached to the ferrule, the lead spring extending outside the distal end of ferrule but still within the distal end of the steering shaft for bending the distal end of the steering shaft in response to an applied force relative to the ferrule;
   a steering wire extending through the lumen, said steering wire having a first end attached to the lead spring at a location outside the distal end of the ferrule and having a second end exiting the proximal end; and
   a controller positioned at the proximal end and attached to the second end of said steering wire for placing tension on said steering wire for applying force to said steering wire to bend the distal end of the steering shaft toward said tensed steering wire, the controller comprising
   a housing connected to the steering shaft;
   a control element mounted in the housing, with the second end of said steering wire being attached to the control element; and
   a manually movable knob for placing tension on said steering wire by operating the control element.

7. A steering mechanism comprising:
   a steering shaft having a proximal end and a distal end and a lumen therethrough;
   a ferrule mounted in the steering shaft and having a distal end that terminates within the steering shaft short of the distal end of the steering shaft;
   a lead spring attached to the ferrule, the lead spring extending outside the distal end of ferrule but still within the distal end of the steering shaft for bending the distal end of the steering shaft in response to an applied force relative to the ferrule;

a steering wire extending through the lumen, said steering wire having a first end attached to the lead spring at a location outside the distal end of the ferrule and having a second end exiting the proximal end; and a controller positioned at the proximal end and attached to said second steering wire end for placing tension on said steering wire for applying force to said steering wire to bend the distal end of the steering shaft toward the tensed steering wire, the controller comprising a housing connected to the steering shaft;

control element means mounted in the housing, with the second end of said steering wire being attached to the control element means, the control element means being operable for placing tension on said steering wire; and a manually movable element accessible outside the housing and attached to the control element means for placing tension on the steering wire by operation of the control element means.

* * * * *